US00PP14703P2

(12) United States Plant Patent
Pierce

(10) Patent No.: US PP14,703 P2
(45) Date of Patent: Apr. 20, 2004

(54) CALIBRACHOA PLANT NAMED 'CAL BULE'

(50) Latin Name: *Calibrachoa sp.*
Varietal Denomination: Cal Bule

(75) Inventor: Robert Osteen Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 63 days.

(21) Appl. No.: 10/400,025

(22) Filed: Mar. 25, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—A. Para
(74) *Attorney, Agent, or Firm*—Jondle & Associates, PC

(57) ABSTRACT

'Cal Blu' is a new variety of Calibrachoa plant. This new variety has blue colored flowers.

1 Drawing Sheet

Genus and species: Calibrachoa sp.
Variety denomination: 'Cal Bule'.

BACKGROUND OF THE INVENTION

'Cal Bule' originated from a hybridization made in the year 2000 in Gilroy, Calif. The female parent was a Calibrachoa breeding line with lavender colored flowers known as 97-2 a proprietary line unnamed and unpatented. The male parent was Calibrachoa variety 114-1, a blue proprietary line unnamed and unpatented.

'Cal Bule' is a product of a planned breeding program intended to create new calibrachoa plants with blue colored flowers, compact habit, good basal branching and moderately vigorous growth.

The new cultivar was created in 2000 in Gilroy, Calif. and has been asexually reproduced repeatedly by vegetative cuttings and tissue culture in Gilroy, Calif., Andijk, The Netherlands, and Guatemala over a 2-year period. The plant has also been trialed at Gilroy, Calif., Litchfield, Mich. and Andijk, The Netherlands. The present invention has been found to retain its distinctive characteristics through successive propagations; and this novelty is firmly fixed.

DESCRIPTION OF THE GENUS CALIBRACHOA LLAVE & LEX.

The genus Petunia was originally established in 1803 by A. L. Jussieu, who described both *P. parviflora* and *P. nyctaginifloa* as type species. Using a non-horticultural system that selected the first mentioned species as the type species (lectotype), N. L. Britton and H. A. Brown declared *P. parviflora* as the type species for Petunia in 1913.

During the 1980's and 1990, H. J. Wijsman published a series of articles regarding the ancestry of P. hybrida, the Garden Petunia, and the inter-relationship of several species classified as Petunia. These studies discovered that P. hybrida and its ancestrial species, *P. nyctaginiflora* (=*P. axillaris*) and *P. violacea* (=*P. integrifolia*), possessed 14 pairs of chromosomes while several other species, including *P. parviflora*, possessed 18 pairs of chromosomes. Since *P. parviflora* was the lectotype species for the Petunia genus, Wijsman and J. H. de Jong proposed transferring the 14 chromosome species to the genus Stimoryne. Horticulturists opposed reclassifying the Garden Petunia and in 1986, Wijsman proposed the alternative of making *P. nyctaginiflora* the lectotype species for Petunia and transferring the 18 chromosome species to another genus. The I. N. G. Committee adopted this proposal. By 1990 Wijsman had transferred several species, including *P. parviflora* (=*C. parviflora*) to Calibrachoa, originally established by Llave and Lexarza in 1825. *Calibrachoa parviflora* (=*C. mexicana* Llave & Lexarza) is now the type species for the genus Calibrachoa.

Classification of the current Petunia and Calibrachoa species is still in progress. New species are also being identified. Consequently a proper description has not been written for the Calibrachoa genus. Calibrachoa can, however, be distinguished from Petunia based on the higher chromosome number, chromosome morphology, plant branching habit and type of flower bud aestivation. Whereas Petunia species bear a flower peduncle and one new stem from a node, Calibrachoa bear a flower peduncle and three stems. Petunia species have a cochlear corolla bud, a single outermost petal covers the other four, radially folded and terminally contorted petals. Calibrachoa flower buds are flat with all five petals linearly folded and the two lower petals forming a cover around the three other petals and fused together.

DETAILED DESCRIPTION OF THE NEW PLANT

The following traits and characteristics describe the new variety. The plant history was taken on 6 month old plants that were cut back numerous times prior to data readings being taken.

Classification:
- *Family.*—Solanaceae.
- *Species.*—*Calibrachoa spp.*

Growth:
- *Form.*—Semi upright and decumbent.
- *Habit.*—Good vigorous habit, well branched, full plant.
- *Height.*—10–15 cm.
- *Width.*—55–65 cm.
- *Time to produce a finished flowering plant.*—8–10 weeks.
- *Outdoors plant performance.*—Full sun, free flowering through the summer, some heat tolerance, used as a hanging basket, in mixed container plantings, flower boxes, mass planting in a bed.

*Time to initiate and develop roots.*—18–23 days.

*Rood description.*—White, fibrous.

Stems:

*Stem color.*—RHS N144C (yellow-green).

*Stem length.*—40–50 cm.

*Stem diameter.*—0.15–0.2 cm.

*Stem internodes length.*—0.5–0.7 cm.

*Stem texture.*—Many glandular hairs various sizes.

*Stem anthocyanin.*—Some very weak blotches.

*Pedicel color.*—Between RHS 144A/B (yellow-green).

*Pedicel length.*—2.5–2.7 cm.

*Pedicel diameter.*—0.1 cm.

*Pedicel texture.*—Many short glandular hairs.

Leaves:

*Arrangement.*—Alternate, upper leaves sub-opposite.

*Leaf color.*—Upper side, between RHS 137A/B (green). Underside, RHS 138A (green).

*Leaf length.*—3.2–4.0 cm.

*Leaf width.*—1.0–1.4 cm.

*Leaf blade shape.*—Elliptic.

*Leaf margin.*—Entire.

*Leaf apex aspect.*—Obtuse.

*Leaf bas aspect.*—Acuminate.

*Leaf texture.*—Short glandular hairs.

*Venation.*—Pinnate.

*Venation color.*—RHS 144B (yellow-green).

*Petiole color.*—RHS 144C (yellow-green).

*Petiole length.*—0.2 cm.

*Petiole width.*—0.1–0.15 cm.

*Petiole texture.*—Many very short glandular hairs.

Bud:

*Color at tight bud.*—RHS 156C (greyed-white), RHS 59A (red-purple) veining.

*Bud shape.*—Oblong.

*Bud diameter.*—0.3–0.4 cm.

*Bud length.*—1.5–1.8 cm.

Flowers:

*Blooming habit.*—Continuous throughout the growing season. Good floriferousness.

*Inflorescence type.*—Flowers solitary in upper leaf axis.

*Floret type.*—Funnel form, 5 lobed petals, fused at base.

*Young flower color.*—RHS N81A/B (purple-violet).

*Young flower floret diameter.*—2.3–2.9 cm.

*Mature flower color.*—Front side, between RHS N87B/C (violet) base color; RHS 83A (violet) mid-veins.

*Mature flower color.*—Underside, RHS 85C (violet); RHS N77D (purple) mid-veins.

*Corolla tube color inside.*—RHS 14C (yellow-orange) base color; RHS 165A (greyed-orange) veining of various intensities.

*Corolla tube length.*—1.5 cm.

*Corolla outside texture.*—Very short glandular hairs.

*Flower (limb) diameter.*—3.5–3.8 cm.

*Petal apex shape.*—Retuse.

*Petal base shape.*—Fused.

*Petal margin.*—Entire.

*Waviness of petals.*—None.

*Petal lobation.*—Weak.

*Petal texture.*—Papillose.

*Sepals.*—5.

*Sepal color.*—RHS 138A (green).

*Sepal length.*—0.8–1.0 cm.

*Sepal width.*—0.25–0.4 cm.

*Sepal shape.*—Oblong.

*Sepal apex.*—Acute.

*Sepal texture.*—Very short glandular hairs.

*Lastingness of individual blooms.*—5–8 days.

*Fragrance.*—None.

Reproductive organs:

*Stamens.*—4.

*Filament color.*—RHS 4D (yellow).

*Pollen color.*—RHS 8B (yellow).

*Pistil.*—One.

*Stigma color.*—RHS 144B (yellow-green).

*Style color.*—RHS 145B (yellow-green).

*Fruit seed set.*—Not observed.

COMPARISION WITH MOST SIMILAR VARIETY

'Cal Bule' differs from the female parent 97-2 in the following ways: 'Cal Bule' has a blue flower and 97-2 has a lavender flower. 'Cal Bule' is earlier to flower and has larger flowers than 97-2.

'Cal Bule' differs from the male parent 114-1 in the following ways: 'Cal Bule' has longer internodes than 114-1. 'Cal Bule' has flowers, which are lighter shade of blue, and has larger leaves than 114-1.

What is claimed is:

1. A new and distinct Calibrachoa plant as shown and described herein.

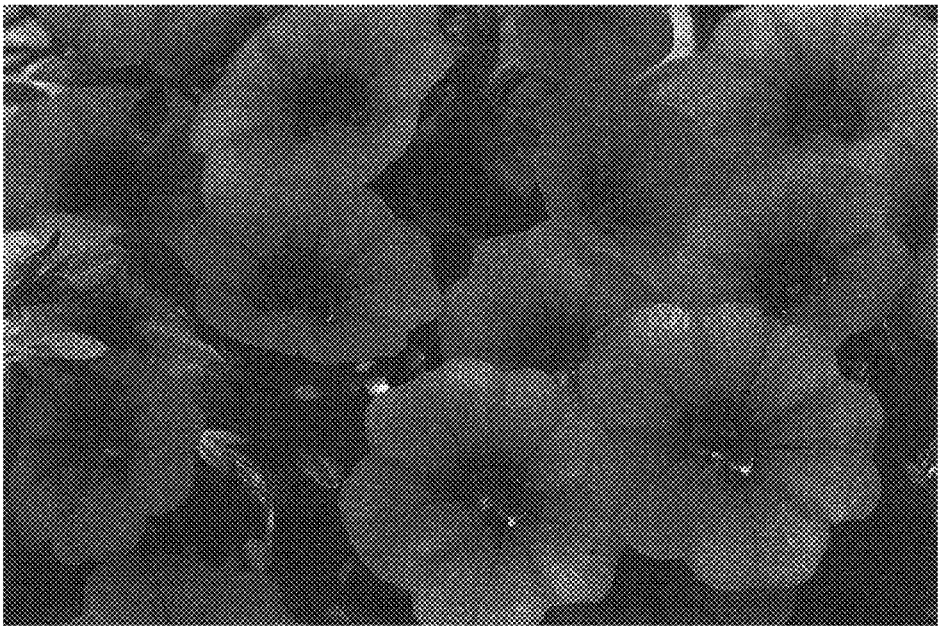

* * * * *